(12) United States Patent
Dupuis

(10) Patent No.: US 6,440,404 B1
(45) Date of Patent: Aug. 27, 2002

(54) AQUEOUS LACQUER FOR TREATING KERATIN SUBSTANCES, PACKAGED IN AN AEROSOL DEVICE AND COMPRISING AT LEAST ONE GRAFTED SILICONE POLYMER, AND USES THEREOF

(75) Inventor: Christine Dupuis, Paris (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/783,959

(22) Filed: Feb. 16, 2001

Related U.S. Application Data

(63) Continuation of application No. 09/051,779, filed as application No. PCT/FR96/01571 on Sep. 2, 1998, now Pat. No. 6,350,439.

(30) Foreign Application Priority Data

Oct. 18, 1995 (FR) .............................. 95 12234

(51) Int. Cl.$^7$ .............................. A61K 7/06; A61K 7/11
(52) U.S. Cl. ................ 424/70.12; 424/70.1; 424/70.11; 424/70.16; 424/43; 424/45; 424/47
(58) Field of Search .............................. 424/70.1, 70.11, 424/70.12, 70.16, 70.2, 43, 45, 47

(56) References Cited

U.S. PATENT DOCUMENTS

| | | | |
|---|---|---|---|
| 4,693,935 A | 9/1987 | Mazurek ...................... 428/352 |
| 4,728,571 A | 3/1988 | Clemens et al. ............. 428/352 |
| 4,972,037 A | 11/1990 | Garbe et al. ................. 526/245 |
| 5,166,276 A | 11/1992 | Hayama et al. ........... 525/329.7 |
| 5,362,485 A | 11/1994 | Hayama et al. |
| 5,441,728 A | 8/1995 | Tsaur et al. ............... 424/70.11 |
| 5,472,689 A | 12/1995 | Ito ........................ 424/70.122 |
| 5,480,634 A | 1/1996 | Hayama et al. .......... 424/70.12 |
| 5,567,428 A | 10/1996 | Hughes ....................... 424/401 |
| 5,618,524 A | 4/1997 | Bolich, Jr. et al. |
| 6,011,126 A | * 1/2000 | Dubief et al. ................ 525/477 |

FOREIGN PATENT DOCUMENTS

| | | |
|---|---|---|
| EP | 0 388 582 | 9/1990 |
| EP | 0 408 311 | 1/1991 |
| EP | 0 412 704 | 2/1991 |
| EP | 0 412 707 | 2/1991 |
| EP | 0 524 612 | 1/1993 |
| EP | 0 582 152 | 2/1994 |
| FR | 2 697 160 | 4/1994 |
| FR | 2 709 955 | 3/1995 |
| FR | 95-11487 | 9/1995 |
| JP | 3-128311 | 5/1991 |
| JP | 6-92825 | 4/1994 |
| WO | WO 93/03703 | 3/1993 |
| WO | WO 93/03704 | 3/1993 |
| WO | WO 93/23009 | 11/1993 |
| WO | WO 93/23446 | 11/1993 |
| WO | WO 95/00108 | 1/1995 |
| WO | WO 95/00578 | 1/1995 |
| WO | WO 95/03776 | 2/1995 |
| WO | WO 95/05800 | 3/1995 |

OTHER PUBLICATIONS

English Language Derwent Abstract of FR 2 697 160, Apr. 1994.

English Language Derwent Abstract of FR 2 709 955, Mar. 1995.

* cited by examiner

*Primary Examiner*—James M. Spear
*Assistant Examiner*—Rachel M. Bennett
(74) *Attorney, Agent, or Firm*—Finnegan, Henderson, Farabow, Garrett & Dunner, L.L.P.

(57) ABSTRACT

A composition for treating keratinous materials, particularly human hair, is disclosed, The composition is packaged in an aerosol device and forms a lacquer at the outlet of the device. Said composition contains (a) at least one silicone graft polymer including a polysiloxane portion and a portion consisting of a non-silicone organic chain, where one of said portions forms the main polymeric chain while the other is grafted onto said main chain; (b) at least 30 wt % of water, (c) at least one propellant; and (d) an organic solvent in an amount of 0–25 wt %; the above percentages by weight being based on the total weight of the composition in the aerosol. Such aqueous lacquers are useful for fixing and/or styling and/or conditioning hair.

60 Claims, No Drawings

AQUEOUS LACQUER FOR TREATING KERATIN SUBSTANCES, PACKAGED IN AN AEROSOL DEVICE AND COMPRISING AT LEAST ONE GRAFTED SILICONE POLYMER, AND USES THEREOF

This is a continuation of application Ser. No. 09/051,779, filed Sep. 2, 1998, now, U.S. Pat. No. 6,350,439, which is the National Stage Application of PCT/FR96/01571, filed Oct. 8, 1996, all of which are incorporated herein by reference.

The present invention relates to an aqueous composition for treating keratin substances, in particular human hair, in the form of a lacquer packaged in an aerosol device for producing a lacquer, comprising a small amount of organic solvent and at least one grafted silicone polymer comprising a polysiloxane portion and a portion consisting of a non-silicone organic chain, one of the two portions constituting the main chain of the polymer, the other being grafted onto the said main chain.

In the text hereinbelow, the term "lacquer" is understood to refer to any composition coming from the outlet of a spray device in the form of liquid droplets sprayed directly onto the keratin support.

Polymers of the grafted silicone polymer type comprising a polysiloxane portion and a portion consisting of a non-silicone organic chain, one of the two portions constituting the main chain of the polymer and the other being grafted onto the said main chain, are known for their styling properties. They are particularly advantageous in hair cosmetics on account of the fact that they give the hair hold.

For a certain number of years, quite specific interest has arisen in aerosol lacquers as a means of packaging formulations for maintaining the hairstyle and/or shaping the hairstyle. Aerosol lacquers containing grafted silicone polymers as described above are generally alcoholic and more preferably aqueous-alcoholic and generally also contain a surfactant. These compositions, containing more than 25% by weight of organic solvent, have a tendency, after the said polymers have been deposited, of leading to phenomena of foaming, giving insufficient sheen properties, giving fixing powers that are not entirely sufficient and making the hair lank (charge effects).

The Applicant has found, surprisingly, that the use of a polymer of the grafted silicone polymer type comprising a polysiloxane portion and a portion consisting of a non-silicone organic chain, one of the two portions constituting the main chain of the polymer and the other being grafted onto the said main chain, in an aqueous lacquer, pressurized in an aerosol device, comprising at least 30% by weight of water and not more than 25% by weight of organic solvent, after application and drying, makes it possible to improve the sheen of the hair and to have a better lacquering power. In addition, this use makes it possible to substantially reduce the charge effects on the hair, or even to eliminate them altogether.

The Applicant has also observed that the pressurized aqueous lacquers in accordance with the invention do not lead to phenomena of foaming on the hair, resulting in a whitening effect, or to phenomena of powdering or smearing. They also provide good styling and restyling properties, good hold to the hair and easy disentangling.

The aqueous composition according to the present invention, packaged in an aerosol device and producing a lacquer at the device outlet, is characterized in that it comprises:

(a) at least one grafted silicone polymer comprising a polysiloxane portion and a portion consisting of a non-silicone organic chain, one of the two portions constituting the main chain of the polymer, the other being grafted onto the said main chain;

(b) at least 30% by weight of water;

(c) at least one propellant;

(d) an amount of organic solvent ranging from 0 to 25% by weight; the weight percentages being defined relative to the total weight of the composition in the aerosol.

The grafted silicone polymers according to the invention are preferably chosen from polymers containing a non-silicone organic skeleton grafted with monomers containing a polysiloxane, polymers containing a polysiloxane skeleton grafted with non-silicone organic monomers and mixtures thereof.

In the following text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bond $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reactive with the said functionalized groups.

One particular family of grafted silicone polymers which is suitable for carrying out the present invention consists of silicone grafted copolymers comprising:

a) from 0 to 98% by weight of at least one lipophilic monomer (A) of low lipophilic polarity containing ethylenic unsaturation, which is polymerizable via a radical route;

b) from 0 to 98% by weight of at least one polar hydrophilic monomer (B) containing ethylenic unsaturation, which is copolymerizable with the (A)-type monomer(s);

c) from 0.01 to 50% by weight of at least one polysiloxane macromer (C) of general formula:

$$X(Y)_n Si(R)_{3-m} Z_m \quad (I)$$

where:
X denotes a vinyl group which is copolymerizable with the monomers (A) and (B);
Y denotes a divalent bonding group;
R denotes a hydrogen, a $C_1$–$C_6$ alkyl or alkoxy or a $C_6$–$C_{12}$ aryl;
Z denotes a monovalent polysiloxane unit having a number-average molecular weight of at least 500;
n is 0 or 1 and m is an integer ranging from 1 to 3; the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic or methacrylic acid esters of 1,1-dihydroperfluoroalkanols or of homologues thereof; acrylic or methacrylic acid esters of ω-hydridofluoroalkanols; acrylic or methacrylic acid esters of fluoroalkylsulphoamidoalcohols; acrylic or methacrylic acid esters of fluoroalkyl alcohols; acrylic or methacrylic acid esters of fluoroether alcohols; or mixtures thereof.

The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (I) are chosen from those corresponding to the general formula (II) below:

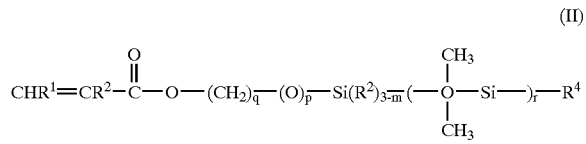

(II)

in which:

$R^1$ is hydrogen or —COOH (preferably hydrogen);

$R^2$ is hydrogen, methyl or —$CH_2COOH$ (preferably methyl);

$R^3$ is $C_1$–$C_6$ alkyl, alkoxy or alkylamino, $C_6$–$C_{12}$ aryl or hydroxyl (preferably methyl);

$R^4$ is $C_1$–$C_6$ alkyl, alkoxy or alkylamino, $C_6$–$C_{12}$ aryl or hydroxyl (preferably methyl);

q is an integer from 2 to 6 (preferably 3);

p is 0 or 1;

r is an integer from 5 to 700;

m is an integer ranging from 1 to 3 (preferably 1).

The polysiloxane macromers of formula:

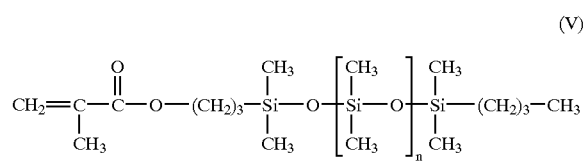

(V)

with n being a number ranging from 5 to 700, are more particularly used.

One particular embodiment of the invention consists in using a copolymer which can be obtained by radical polymerization starting with the monomer mixture consisting of:

a) 60% by weight of tert-butyl acrylate;
b) 20% by weight of acrylic acid;

c) 20% by Weight of silicone macromer of formula:

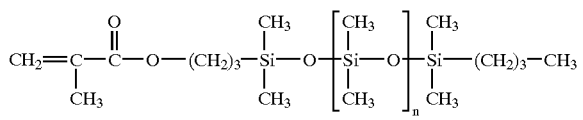
(V)

with n being a number ranging from 5 to 700; the weight percentages being calculated relative to the total weight of the monomers.

Another particular embodiment of the invention consists in using a copolymer which can be obtained by radical polymerization start ng with the monomer mixture consisting of:

a) 80% by weight of tert-butyl acrylate;
b) 20% by weight of silicone macromer of formula:

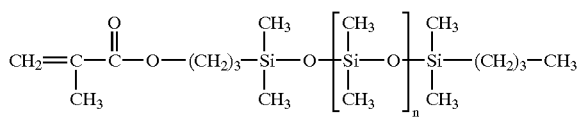
(V)

with n being a number ranging from 5 to 700; the weight percentages being calculated relative to the total weight of the monomers.

Another particular family of silicone polymers which is suitable for carrying out the present invention consists of silicone grafted copolymers which can be obtained by reactive extrusion of a polysiloxane macromer having a terminal reactive function, with a polyolefin-type polymer containing reactive groups which can react with the terminal function of the polysiloxane macromer in order to form a covalent bond which allows the silicone to be grafted onto the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth) acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula (III):

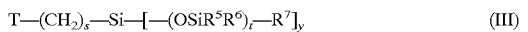
(III)

in which T is chosen from the group consisting of $NH_2$, NHR', an epoxy, OH, or SH function; $R^5$, $R^6$, $R^7$ and R' independently denote a $C_1$–$C_6$ alkyl, phenyl, benzyl, $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and more particularly from 9000 to 40,000.

According to the present invention, the grafted silicone polymer(s) containing a polysiloxane skeleton grafted with non-silicone organic monomers comprise a silicone (or polysiloxane ($\equiv$Si—O—)$_n$) main chain on which is grafted, inside the said chain and optionally on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of polymers containing a polysiloxane skeleton grafted with non-silicone organic monomers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer containing a polysiloxane skeleton grafted with non-silicone organic monomers, which is used, comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) unsaturated carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo)polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (IV) below:

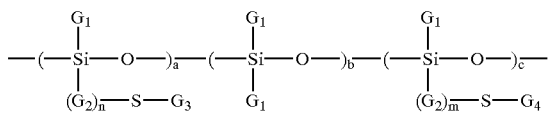

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) above has at least one, and even more preferably all, of the following characteristics:
  the radicals $G_1$ denote an alkyl radical, preferably the methyl radical;
  n is non-zero and the radicals $G_2$ represent a divalent $C_1$–$C_3$ radical, preferably a propylene radical;
  $G_3$ represents a polymeric radical resulting from the (homo)polymerization of at least one monomer of the carboxylic acid type containing ethylenic unsaturation, preferably acrylic acid and/or methacrylic acid;
  $G_4$ represents a polymeric radical resulting from the (homo)polymerization of at least one monomer of the $C_1$–$C_{10}$ alkyl (meth)acrylate type, preferably isobutyl or methyl (meth)acrylate.

Examples of grafted silicone polymers corresponding to formula (IV) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of grafted silicone polymers corresponding to formula (IV) are, in particular, polydimethylsiloxanes (PDMS) on which are grafted, via a thiopropylene-type connecting chain, polymer units of the polyisobutyl (meth)acrylate type.

Preferably, the number-average molecular mass of the silicone polymers containing a polysiloxane skeleton grafted with non-silicone organic monomers, or the invention, ranges approximately from 10,000 to 1,000,000 and even more preferably approximately from 10,000 to 100,000.

The grafted silicone polymers of the invention are preferably used in an amount ranging from 0.01 to 20% by weight relative to the total weight of the composition. More preferably, this amount ranges from 0.1 to 15% by weight and even more preferably from 0.5 to 10% by weight.

The grafted silicone polymers of the invention can be dissolved in the aqueous medium of the aerosol lacquer or used in the form of an aqueous dispersion of particles.

The compositions according to the invention preferably contain from 45 to 100% of water relative to the total weight of the composition in the aerosol, and more particularly from 60 to 99.5% of water.

The organic solvents which can be used in the aerosol compositions of the invention are preferably chosen from $C_1$–$C_4$ alcohols such as, for example, ethanol and isopropanol.

The organic solvents are present in the aerosol compositions in concentrations preferably ranging up to 10% by weight relative to the total weight of the composition in the aerosol, and more particularly up to 5% by weight. The case corresponding to the total absence of organic solvent is most particularly advantageous.

The compositions according to the invention, packaged in aerosol form in order to obtain a lacquer, comprise a propellant which may be chosen from the group consisting of volatile hydrocarbons such as n-butane, propane, isobutane and pentane; chlorinated and/or fluorinated hydrocarbons and mixtures thereof. Carbon dioxide, nitrous oxide, dimethyl ether, nitrogen, compressed air and mixtures thereof can also be used as propellant. Dimethyl ether is particularly preferred.

The concentration of the propellent gas in the aerosol device depends on the nature of the propellant chosen. It is used in the aerosol compositions of the invention in concentrations preferably ranging from 10 to 68% by weight relative to the total weight of the composition in the aerosol device, and more particularly from 25 to 50% by weight.

The concentration of volatile organic compound (VOC) in a composition according to the invention packaged in aerosol form is preferably less than or equal to 55% by weight relative to the total weight of the formulation packaged as an aerosol.

The pH of the compositions according to the invention is generally between 2 and 9 and in particular between 3 and 8. It can be adjusted to the chosen value by means of basifying or acidifying agents usually used in cosmetics.

The hair compositions in accordance with the invention can also contain conventional cosmetic additives such as preserving agents, softeners, sequestering agents, fragrances, viscosity modifiers, pearlescent agents, moisturizers, antidandruff agents, antiseborrhoeic agents, sunscreens, hair conditioners, antioxidants, proteins, vitamins, silicones and polymers. In particular, the compositions of the invention can also contain anionic, cationic, amphoteric or nonionic styling polymers with hair-fixing properties.

One of the advantages of the compositions according to the invention over the aqueous aerosol lacquers of the prior art containing silicone grafted polymers is that they can be free of any surfactant.

The compositions according to the invention as defined above can be used as styling products for shaping and/or maintaining the hairstyle and/or for conditioning the hair.

Another subject of the invention consists of a non-therapeutic process for shaping and/or maintaining the hair and/or for conditioning the hair, characterized in that it consists in applying a composition as defined above directly to the hair.

The examples which follow serve to illustrate the invention without, however, being limiting in nature.

EXAMPLE 1

Aerosol Lacquer Containing 55% VOCs (Volatile Organic Compounds)

| | | |
|---|---|---|
| Grafted silicone polymer of formula (IV) of polymethyl/methyl-siloxane structure containing 3-propylthio polymethacrylic acid groups and 3-propylthio polymethyl methacrylate groups | 5 g | AM |
| Aminomethylpropanol, qs 100% neutralization | | |
| Ethanol | 20 g | |
| Demineralized water | 40 g | |
| Dimethyl ether | 35 g | |

EXAMPLE 2

Aerosol Lacquer Containing 30% VOCs

| | | |
|---|---|---|
| Grafted silicone polymer of formula (IV) of polymethyl/methylsiloxane structure containing 3-propylthio polymethacrylic acid groups and 3-propylthio polymethyl methacrylate groups | 7 mg | AM |
| Aminomethylpropanol, qs 100% neutralization | | |
| Demineralized water | 63 g | |
| Dimethyl ether | 30 g | |

EXAMPLE 3

Aerosol Lacquer Containing 55% VOCs

| | | |
|---|---|---|
| Grafted silicone polymer of structure (1) as defined below | 3 g | AM |
| Aminomethylpropanol qs | | |
| Ethanol | 17 g | |
| Demineralized water | 42 g | |
| Dimethyl ether | 38 g | |

Structure (1)

Copolymer obtained by radical polymerization from the monomer mixture consisting of:

a) 60% by weight of tert-butyl acrylate;

b) 20% by weight of acrylic acid;

c) 20% by weight of silicone macromer of formula:

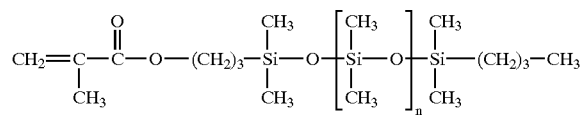

(V)

with n being a number chosen such that the number-average molecular weight of the macromer is approximately between 9000 and 12,000; the weight percentages being calculated relative to the total weight of the monomers.

Comparative Examples

The 4 aerosol aqueous lacquer formulations A, B, C and D defined in the table below are compared:

| Formulation | A (prior art) | B (invention) | C (invention) | D (invention) |
|---|---|---|---|---|
| Silicone grafted polymer of Examples 1 and 2 | 3 g AM | 3 g AM | 3 g AM | 3 g AM |
| Amino-methyl-propanol | qs neutraliz-ation 100% | qs neutraliz-ation 100% | qs neutraliz-ation 100% | qs neutraliz-ation 100% |
| Water | 20 g | 42 g | 42 g | 67 g |
| Ethanol | 47 g | 25 g | 25 g | — |
| Dimethyl ether | 15 g | 15 g | 30 g | 30 g |
| Isobutane/propane/butane mixture (23/55/22) | 15 g | 15 g | — | — |

A sensory evaluation test was carried out on a panel of 5 individuals. The lacquering power on the hair after application and drying, the powdering effect after disentangling fixed hair and the sheen after disentangling are studied, as cosmetic criteria, for each aerosol lacquer A, B, C and D.

Each lacquer tested is vaporized for 10 sec on a 5 g sample of locks of hair spread out on a support.

The 5 individuals questioned found that compositions B, C and D according to the invention, containing more than 40% by weight of water and not more than 25% by weight of organic solvent, had a better lacquering power, better sheen and a lower dusting effect than the composition A according to the prior art containing more than 25% by weight of organic solvent (47%). Furthermore, lacquer A leads, after spraying, to white traces on the hair when dried (foaming effect), in contrast with the compositions B, C and D of the invention.

What is claimed is:

1. An aqueous composition for treating a keratin substance comprising:

(a) at least one grafted silicone polymer selected from (1) a polymer containing a non-silicone organic skeleton grafted with monomers containing a polysiloxane, and (2) a polymer containing a polysiloxane skeleton grafted with non-silicone organic monomers, provided that the composition does not contain both grafted silicone polymer (1) and grafted slicone polymer (2);

(b) at least 30% by weight of water;

(c) at least one propellant; and (d) at least one organic solvent in an amount ranging from 0 to 25% by weight;

wherein the weight percentages are relative to the total weight of said composition, and further wherein said composition is packaged in an aerosol device; and provided that the at least one grafted silicone polymer is formed from a monomer mixture comprising a polysiloxane macromer other than that of formula V:

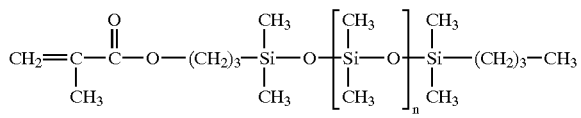

in which n is a number ranging from 5 to 700.

2. An aqueous composition according to claim 1, wherein said composition is expelled from said aerosol device as a lacquer.

3. An aqueous composition according to claim 1, wherein said at least one grafted silicone polymer comprises a non-silicone organic main chain on which is grafted, inside said chain and optionally on at least one of its ends, at least one polysiloxane macromer.

4. An aqueous composition according to claim 3, wherein said non-silicone organic main chain comprises monomeric residues formed from monomers selected from monomers containing ethylenic unsaturation polymerizable via a radical route, monomers polymerizable by polycondensation and monomers which involve ring opening.

5. An aqueous composition according to claim 1, wherein said at least one grafted silicone polymer comprising a non-silicone organic skeleton grafted with monomers containing a polysiloxane is selected from polymers obtained by radical polymerization of monomers containing ethylenic unsaturation and silicone macromers having a terminal vinyl group or polymers obtained from reacting a polyolefin comprising functionalized groups with a polysiloxane macromer having a terminal function reactive with said functionalized groups.

6. An aqueous composition according to claim 1, wherein said composition comprises at least one grafted silicone copolymer formed:
   a) from 0 to 98% by weight of at least one lipophilic monomer (A) of low polarity containing ethylenic unsaturation of low polarity, polymerizable via a radical route;
   b) from 0 to 98% by weight of at least one polar hydrophilic monomer (B) containing ethylenic unsaturation, copolymerizable with said (A) monomer;
   c) from 0.01 to 50% by weight of at least one polysiloxane macromer (C) of formula (I):

in which:
   X denotes a vinyl group copolymerizable with said monomers (A) and (B);
   Y denotes a divalent bonding group;
   R denotes a hydrogen, a $C_1$–$C_6$ alkyl or alkoxy or a $C_6$–$C_{12}$ aryl;
   Z denotes a monovalent polysiloxane unit having a number-average molecular weight of at least 500;
   n is 0 or 1; and
   m is an integer ranging from 1 to 3;
wherein the percentages are calculated relative to the total combined weight of said monomers (A), (B) and (C).

7. An aqueous composition according to claim 6, wherein said at least one grafted silicone copolymer has a number-average molecular weight ranging from 10,000 to 2,000,000 and a glass transition temperature (Tg) or a crystalline melting point (Tm) of at least 20° C.

8. An aqueous composition according to claim 6, wherein said at least one lipophilic monomer (A) is selected from acrylic and methacrylic acid esters of $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic and methacrylic acid esters of 1,1-dihydroperfluoroalkanols and homologues thereof; acrylic and methacrylic acid esters of ω-hydridofluoroalkanols; acrylic and methacrylic acid esters of fluoroalkylsulphoamidoalcohols; acrylic and methacrylic acid esters of fluoroalkyl alcohols; and acrylic and methacrylic acid esters of fluoroether alcohols.

9. An aqueous composition according to claim 8, wherein said at least one lipophilic monomer (A) is selected from n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(butylperfluorooctanesulphonamido)ethyl acrylate.

10. An aqueous composition according to claim 6, wherein said at least one polar monomer (B) is selected from acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam.

11. An aqueous composition according to claim 10, wherein said at least one polar monomer (B) is selected from acrylic acid, N,N-dimethylacrylamide, dimethylaminoethyl methacrylate, quaternized dimethylaminoethyl methacrylate and vinylpyrrolidone.

12. An aqueous composition according to claim 6, wherein said at least one polysiloxane macromer (C) is selected from formula (II):

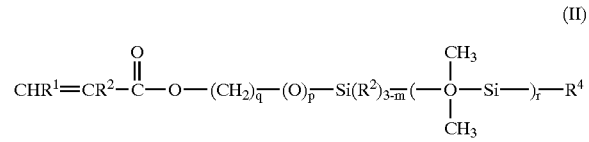

in which:
   $R^1$ is hydrogen or —COOH;
   $R^2$ is hydrogen, methyl or —$CH_2COOH$;
   $R^3$ is $C_1$–$C_6$ alkyl, alkoxy or alkylamino, $C_6$–$C_{12}$ aryl or hydroxyl;
   $R^4$ is $C_1$–$C_6$ alkyl, alkoxy or alkylamino, $C_6$–$C_{12}$ aryl or hydroxyl;
   q is an integer ranging from 2 to 6;
   p is 0 or 1;
   r is an integer ranging from 5 to 700;
   m is an integer ranging from 1 to 3.

13. An aqueous composition according to claim 12, wherein at least one of the following is true:
   $R_1$ is hydrogen;
   $R_2$ is methyl;
   $R_3$ is methyl;
   $R_4$ is methyl;
   q is 3; and
   m is 1.

14. An aqueous composition according to claim 5 wherein said at least one polymer containing a non-silicone organic skeletion grafted with monomers containing a polysilxane is obtained by reactive extrusion of at least one polysiloxane macromer having a terminal reactive function with a polyolefin polymer containing groups which can react with said terminal reactive function of said polysiloxane macromer to form a covalent bond allowing the silicone to be grafted onto the main chain of said polyolefin.

15. An aqueous composition according to claim 14, wherein said reactive polyolefin is selected from polyethylenes and polymers of ethylene-derived monomers.

16. An aqueous composition according to claim 15, wherein said reactive polyolefin is selected from copolymers of ethylene or of ethylene derivatives and of monomers selected from monomers containing a carboxylic function, monomers containing an acid anhydride function, monomers containing an acid chloride function, monomers containing an ester function, and monomers containing an isocyanate function.

17. An aqueous composition according to claim 5, wherein said polysiloxane macromer is a polysiloxane containing a functionalized group, at the end of the polysiloxane chain or close to the end of said chain, selected from alcohols, thiols, epoxy groups and primary and secondary amines.

18. An aqueous composition according to claim 17, wherein said polysiloxane macromer is selected from formula (III):

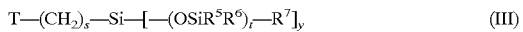

in which
T is selected from $NH_2$, NHR', an epoxy, OH, and SH function;
$R^5$, $R^6$, $R^7$ and R' independently denote a $C_1$–$C_6$ alkyl, phenyl, benzyl, $C_6$–$C_{12}$ alkylphenyl or hydrogen;
s is a number from 2 to 100;
t is a number from 0 to 1000 and
y is a number from 1 to 3.

19. An aqueous composition according to claim 18, wherein said polysiloxane macromer has a number-average molecular weight ranging from 5000 to 300,000.

20. An aqueous composition according to claim 19, wherein said polysiloxane macromer has a number-average molecular weight ranging from 8000 to 200,000.

21. An aqueous composition according to claim 20, wherein said polysiloxane macromer has a number-average molecular weight ranging from 9000 to 40,000.

22. An aqueous composition according to claim 1, wherein said at least one grafted silicone polymer comprises a main polysiloxane main chain on which is grafted, inside said chain and optionally on at least one of its ends, at least one organic group containing no silicone.

23. An aqueous composition according to claim 22, wherein said at least one grafted silicone polymer is obtained by radical copolymerization of:
at least one non-silicone anionic organic monomer having ethylenic unsaturation and/or at least one non-silicone hydrophobic organic monomer having ethylenic unsaturation, and
at least one polysiloxane having in its chain at least one functional group capable of reacting with said ethylenic unsaturations of said non-silicone monomers.

24. An aqueous composition according to claim 23, wherein said at least one functional group is a thio functional group.

25. An aqueous composition according to claim 23, wherein said at least one anionic organic monomer containing ethylenic unsaturation is selected from linear and branched, unsaturated carboxylic acids.

26. An aqueous composition according to claim 25, wherein said at least one anionic organic monomer containing ethylenic unsaturation is selected from acrylic acid, methacrylic acid, maleic acid, maleic anhydride, itaconic acid, fumaric acid and crotonic acid, and alkali metal salts, alkaline-earth metal salts and ammonium salts thereof.

27. An aqueous composition according to claim 23, wherein said at least one hydrophobic organic monomer containing ethylenic unsaturation is selected from acrylic acid esters of alkanol and methacrylic acid esters of alkanol.

28. An aqueous composition according to claim 27, wherein said alkanol is selected from a $C_1$–$C_{18}$ alkanol.

29. An aqueous composition according to claim 27, wherein said alkanol is selected from a $C_1$–$C_{12}$ alkanol.

30. An aqueous composition according to claim 27, wherein said at least one hydrophobic organic monomer containing ethylenic unsaturation is selected from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate.

31. An aqueous composition according to claim 22, wherein said at least one grafted silicone polymer comprises, on the main silicone chain, at least one organic group of anionic nature obtained by radical (homo) polymerization of at least one anionic monomer of unsaturated carboxylic acid type, partially or totally neutralized in the form of a salt.

32. An aqueous composition according to claim 22, wherein said at least one grafted silicone polymer is selected from silicone polymers containing at least one unit of formula (IV):

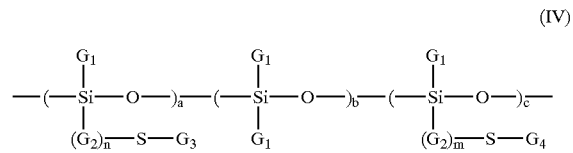

in which:
$G_1$ independently represent hydrogen or a $C_1$–$C_{10}$ alkyl radical or a phenyl radical;
$G_2$ independently represent a $C_1$–$C_{10}$ alkylene group;
$G_3$ represents a polymer residue from the (homo) polymerization of at least one anionic monomer containing ethylenic unsaturation;
$G_4$ represents a polymer residue from the (homo) polymerization of at least one hydrophobic monomer containing ethylenic unsaturation;
m and n are equal to 0 or 1;
a is an integer ranging from 0 to 50;
b is an integer ranging from 10 to 350 and
c is an integer ranging from 0 to 50;
wherein either a or c is not 0.

33. An aqueous composition according to claim 32, wherein at least one of the following is true:
$G_1$ independently denote a $C_1$–$C_{10}$ alkyl radical;
n is not zero;
$G_2$ independently represent a divalent $C_1$–$C_3$ radical;
$G_3$ represents a polymeric radical resulting from the (homo)polymerization of at least one carboxylic acid monomer containing ethylenic unsaturation; and G$_4$ represents a polymeric radical resulting from the (homo)polymerization of at least one C$_1$–C$_{10}$ alkyl (meth)acrylate monomer.

34. An aqueous composition according to claim 33, wherein
G$_1$ denote a methyl radical;
n is not zero;
G$_2$ represent a propylene radical;
G$_3$ represents a polymeric radical resulting from the (homo)polymerization of acrylic acid and/or methacrylic acid; and
G$_4$ represents a polymeric radical resulting from the (homo)polymerization of at least one isobutyl or methyl (meth)acrylate monomer.

35. An aqueous composition according to claim 22, wherein said at least one grafted silicone polymer containing a polysiloxane skeleton grafted with at least one organic group containing no silicone has a number-average molecular mass ranging from 10,000 to 1,000,000.

36. An aqueous composition according to claim 35, wherein said at least one grafted silicone polymer containing a polysiloxane skeleton grafted with at least one organic group containing no silicone has a number-average molecular mass ranging from 10,000 to 100,000.

37. An aqueous composition according to claim 1, wherein said at least one grafted silicone polymer is present in an amount ranging from 0.01 to 20% by weight relative to the total weight of said composition.

38. An aqueous composition according to claim 37, wherein said at least one grafted silicone polymer is present in an amount ranging from 0.1 to 15% by weight relative to the total weight of said composition.

39. An aqueous composition according to claim 38, wherein said at least one grafted silicone polymer is present in an amount ranging from 0.5 to 10% by weight relative to the total weight of said composition.

40. An aqueous composition according to claim 1 wherein said composition comprises from 45 to 99.5% of water relative to the total weight of said composition.

41. An aqueous composition according to claim 40, wherein said composition comprises from 60 to 99.5% of water relative to the total weight of said composition.

42. An aqueous composition according to claim 1, wherein said at least one grafted silicone polymer is dissolved in an aqueous medium or is an aqueous dispersion of particles.

43. An aqueous composition according to claim 1, wherein said at least one organic solvent is selected from a C$_1$–C$_4$ alcohol.

44. An aqueous composition according to claim 43, wherein said at least one organic solvent is selected from ethanol and isopropanol.

45. An aqueous composition according to claim 1, wherein said at least one organic solvent is present in an amount ranging from 0 to 10% by weight relative to the total weight of said composition.

46. An aqueous composition according to claim 45, wherein said at least one organic solvent is present in an amount ranging from 0 to 5% by weight relative to the total weight of said composition.

47. An aqueous composition according to claim 1, wherein said composition comprises no organic solvent.

48. An aqueous composition according to claim 1, wherein said at least one propellant is selected from volatile hydrocarbons; chlorinated and fluorinated hydrocarbons; carbon dioxide, nitrous oxide, dimethyl ether, nitrogen, and compressed air.

49. An aqueous composition according to claim 48, wherein said at least one propellant is dimethyl ether.

50. An aqueous composition according to claim 1, wherein said at least one propellant is present in an amount ranging from 10 to 68% by weight relative to the total weight of said composition.

51. An aqueous composition according to claim 50, wherein said at least one propellant is present in an amount ranging from 25 to 50% by weight relative to the total weight of said composition.

52. An aqueous composition according to claim 1, wherein said at least one propellant is selected from volatile organic compounds (VOC) present in an amount no greater than 55% by weight relative to the total weight of said composition.

53. An aqueous composition according to claim 1, wherein said composition has a pH ranging from 2 to 9.

54. An aqueous composition according to claim 53, wherein said composition has a pH ranging from 3 to 8.

55. An aqueous composition according to claim 1, wherein said composition further comprises at least one adjuvant.

56. An aqueous composition according to claim 55 wherein said at least one adjuvant is selected from preserving agents, softeners, sequestering agents, fragrances, viscosity modifiers, pearlescent agents, moisturizers, antidandruff agents, antiseborrhoeic agents, sunscreens, hair conditioners, antioxidants, proteins, vitamins, silicones, and basifying and acidifying agents for styling anionic, cationic, amphoteric or nonionic polymers with hair-fixing properties.

57. An aqueous composition according to claim 1, wherein said composition is in the form of a hair product.

58. An aqueous composition according to claim 57, wherein said hair product is for maintaining and/or shaping the hair and/or for conditioning the hair.

59. A non-therapeutic process for maintaining and/or shaping hair and/or for conditioning hair, comprising applying to said hair a composition comprising:
(a) at least one grafted silicone polymer selected from (1) a polymer containing a non-silicone organic skeleton grafted with monomers containing a polysiloxane, and (2) a polymer containing a polysiloxane skeleton grafted with non-silicone organic monomers, provided that the composition does not contain both grafted silicone polymer (1) and grafted slicone polymer (2);
(b) at least 30% by weight of water;
(c) at least one propellant; and
(d) at least one organic solvent in an amount ranging from 0 to 25% by weight;
wherein the weight percentages are relative to the total weight of said composition, and further wherein said composition is packaged in an aerosol device; and provided that the at least one grafted silicone polymer is formed from a monomer mixture comprising a polysiloxane macromer other than that of formula V:

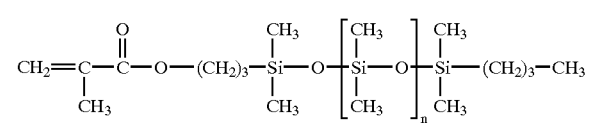

in which n is a number ranging from 5 to 700.

60. A process according to claim 59, wherein said hair is human hair.

\* \* \* \* \*

UNITED STATES PATENT AND TRADEMARK OFFICE
CERTIFICATE OF CORRECTION

PATENT NO. : 6,440,404 B1
DATED : August 27, 2002
INVENTOR(S) : Christine Dupuis It is certified that error appears in the above-identified patent and that said Letters Patent is hereby corrected as shown below:

Column 12,
Formula (II), line 41, "Si($R^2$)$_{3-m}$" should read -- Si($R^2$)$_{3-m}$ --.

Signed and Sealed this

Fourteenth Day of January, 2003

JAMES E. ROGAN
*Director of the United States Patent and Trademark Office*